(12) United States Patent
Eddy

(10) Patent No.: US 10,864,058 B2
(45) Date of Patent: Dec. 15, 2020

(54) ANTIMICROBIAL TREATMENT FOR A SURGICAL HEADLAMP SYSTEM

(71) Applicant: Parasol Medical LLC, Buffalo Grove, IL (US)

(72) Inventor: Patrick E. Eddy, Allendale, MI (US)

(73) Assignee: Parasol Medical, LLC, Buffalo Grove, IL (US)

( * ) Notice: Subject to any disclaimer, the term of this patent is extended or adjusted under 35 U.S.C. 154(b) by 158 days.

(21) Appl. No.: 15/938,934

(22) Filed: Mar. 28, 2018

(65) Prior Publication Data
US 2019/0298479 A1    Oct. 3, 2019

(51) Int. Cl.
*A61B 90/30* (2016.01)
*F21V 21/084* (2006.01)
(Continued)

(52) U.S. Cl.
CPC ............ *A61B 90/30* (2016.02); *F21V 21/084* (2013.01); *A61B 90/36* (2016.02); *A61L 2300/404* (2013.01); *F21L 14/00* (2013.01)

(58) Field of Classification Search
CPC .............................. A61B 90/30; F21V 21/084
See application file for complete search history.

(56) References Cited

U.S. PATENT DOCUMENTS

| | | |
|---|---|---|
| 4,372,303 A | 2/1983 | Grossmann et al. |
| 4,865,844 A | 9/1989 | Blank et al. |

(Continued)

FOREIGN PATENT DOCUMENTS

| | | |
|---|---|---|
| WO | 0054587 A1 | 9/2000 |
| WO | 0072850 A1 | 12/2000 |

(Continued)

OTHER PUBLICATIONS

Anonymous, 2009, SiSiB PC9911 Antimicrobial, Power Chemical Corp, [online]; downloaded from URL<http://www.powerchemcorp.com/library/public/SiSiB_PC9911.pdf> on Oct. 8, 2013; 2 pages.

(Continued)

*Primary Examiner* — Christopher J Beccia
(74) *Attorney, Agent, or Firm* — Price Heneveld LLP

(57) ABSTRACT

A surgical headlight system has a headlamp. The surgical headlight system can further include a headwear structure, configured to be worn on a surgeon's head during surgery, supporting the headlamp. The surgical headlight system can further include a video camera configured to record surgery. The headlamp, the headwear structure and the video camera all have an exterior surface. An antimicrobial coating is applied to the exterior surface of the headlamp, the exterior surface of the video camera, and/or the exterior surface of the headwear structure. The antimicrobial coating includes a silane quaternary ammonium ion or salt thereof. The antimicrobial coating imparts antimicrobial properties onto the exterior surface to which it is applied, such as the exterior surface of the headlamp. The silane quaternary ammonium ion or salt thereof can be one or more of 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride.

15 Claims, 4 Drawing Sheets

(51) Int. Cl.
*A61B 90/00* (2016.01)
*F21L 14/00* (2006.01)

(56) References Cited

U.S. PATENT DOCUMENTS

| | | | |
|---|---|---|---|
| 4,921,691 A | 5/1990 | Stockel | |
| 5,079,004 A | 1/1992 | Blank et al. | |
| 5,183,664 A | 2/1993 | Ansell | |
| 5,270,358 A | 12/1993 | Asmus | |
| 5,428,078 A | 6/1995 | Cohen et al. | |
| 5,762,623 A | 6/1998 | Murphy et al. | |
| 5,954,869 A | 9/1999 | Elfersy et al. | |
| 5,959,014 A | 9/1999 | Liebeskind et al. | |
| 6,224,579 B1 | 5/2001 | Modak et al. | |
| 6,495,229 B1 | 12/2002 | Carte et al. | |
| 6,821,943 B2 | 11/2004 | Avery et al. | |
| 6,994,890 B2 | 2/2006 | Ohlhausen et al. | |
| 7,045,673 B1 | 5/2006 | Batich et al. | |
| 7,704,313 B2 | 4/2010 | Ohlhausen et al. | |
| 7,709,694 B2 | 5/2010 | Batich et al. | |
| 7,754,004 B2 | 7/2010 | Ohlhausen et al. | |
| 7,790,217 B2 | 9/2010 | Toreki et al. | |
| 8,025,120 B2 | 9/2011 | Eddy | |
| 8,257,780 B2 | 9/2012 | Ohlhausen et al. | |
| 8,440,217 B1 | 5/2013 | EL-Naggar et al. | |
| 8,491,922 B2 | 7/2013 | Eddy | |
| 8,639,527 B2 | 1/2014 | Rensvold et al. | |
| 8,679,526 B2 | 3/2014 | Van Den Plas et al. | |
| 9,028,846 B2 | 5/2015 | Eddy | |
| 9,433,708 B2 | 9/2016 | Eddy | |
| 9,675,735 B2 | 6/2017 | Eddy | |
| 9,717,249 B2 | 8/2017 | Eddy | |
| 10,258,411 B1* | 4/2019 | Ferguson | H04N 5/77 |
| 2002/0111282 A1 | 8/2002 | Charaf et al. | |
| 2007/0021383 A1 | 1/2007 | Loder | |
| 2007/0042198 A1 | 2/2007 | Schonemyr et al. | |
| 2007/0218096 A1 | 9/2007 | Wooley | |
| 2008/0260804 A1 | 10/2008 | Morris et al. | |
| 2009/0215917 A1 | 8/2009 | Trotter et al. | |
| 2009/0223411 A1 | 9/2009 | Higgins et al. | |
| 2009/0252647 A1 | 10/2009 | Orofino | |
| 2009/0312684 A1 | 12/2009 | Leonard et al. | |
| 2010/0028462 A1 | 2/2010 | Bolkan et al. | |
| 2010/0167978 A1 | 7/2010 | Iyer et al. | |
| 2010/0331710 A1 | 12/2010 | Eddy | |
| 2011/0200655 A1 | 8/2011 | Black et al. | |
| 2011/0233810 A1 | 9/2011 | Neigel et al. | |
| 2012/0052106 A1* | 3/2012 | Eddy | A01N 33/12 424/409 |
| 2012/0173274 A1 | 7/2012 | Rensvold et al. | |
| 2013/0017242 A1* | 1/2013 | Richardson | A01N 25/34 424/411 |
| 2013/0101677 A1 | 4/2013 | Callahan et al. | |
| 2013/0231599 A1 | 9/2013 | Eddy | |
| 2013/0345170 A1 | 12/2013 | Eddy | |
| 2014/0100504 A1 | 4/2014 | Eddy | |
| 2014/0271794 A1 | 9/2014 | Eddy | |
| 2015/0305343 A1 | 10/2015 | Burke et al. | |
| 2016/0143275 A1 | 5/2016 | Lan et al. | |
| 2016/0143276 A1 | 5/2016 | Lan et al. | |
| 2016/0262382 A1 | 9/2016 | Lan et al. | |
| 2016/0262383 A1 | 9/2016 | Lan et al. | |
| 2017/0280716 A1 | 10/2017 | Lan et al. | |
| 2018/0224674 A1* | 8/2018 | Carabin | G02C 11/10 |

FOREIGN PATENT DOCUMENTS

| | | |
|---|---|---|
| WO | 2005042657 A2 | 5/2005 |
| WO | 2007061625 A2 | 5/2007 |
| WO | 2007076413 A2 | 7/2007 |
| WO | 2008076839 A2 | 6/2008 |
| WO | 2008097599 A2 | 8/2008 |
| WO | 2013102021 A2 | 7/2013 |

OTHER PUBLICATIONS

Murray et al., "Microbial Inhibition on Hospital Garments Treated with Dow Corning 5700 Antimicrobial Agent," Journal of Clinical Microbiology, vol. 26, No. 9, Sep. 1988, pp. 1884-1886.

AEGIS Environments, Material Safety Data Sheet AEGIS Microbe Shield(TM) Program—AEGIS(TM) Antimicrobial (Typical Application Strength), Midland, Michigan USA, May 12, 2004 (5 pages).

Rutala et al., "Guideline for Disinfection and Sterilization in Healthcare Facilities, 2008," Centers for Disease Control (CDC), Department of Health & Human Services, Feb. 15, 2017 (161 pages).

U.S. Food & Drug Administration (FDA), "Reprocessing Medical Devices in Health Care Settings: Validation Methods and Labeling Guidance for Industry and Food and Drug Administration Staff," Mar. 17, 2015 (44 pages).

European Commission, "Aerosol Dispensers Directive Evaluation—Background document", Sep. 23, 2016, Directorate-General for Internal Market, Industry, Entrepreneurship and SMEs, Belgium (1 page).

Monticello, Robert A., "The Use of Reactive Silane Chemistries to Provide Durable, Non-Leaching Antimicrobial Surfaces", AEGIS Environments, Midland, Michigan USA, Jan. 1, 2010 (77 pages).

* cited by examiner

1

ANTIMICROBIAL TREATMENT FOR A SURGICAL HEADLAMP SYSTEM

BACKGROUND OF THE INVENTION

Surgeons sometimes use a surgical headlamp system while performing surgery. The surgical headlamp system includes a headlamp to illuminate the surgical area. The surgical headlamp system typically further includes a headwear structure and various other accessories supported by the headwear structure, such as a video camera. However, the exterior surfaces of the surgical headlamp system may contain harmful bacteria, microbes, viruses, and the like, which can subsequently be transferred to the patient undergoing the surgery.

BRIEF SUMMARY OF THE INVENTION

According to a first aspect of the present disclosure, a surgical headlight system comprises: a headlamp including an exterior surface; and an antimicrobial coating applied to the exterior surface of the headlamp; wherein, the antimicrobial coating includes a silane quaternary ammonium ion or salt thereof.

Embodiments of the first aspect of the invention can include any one or a combination of the following features:
- the silane quaternary ammonium ion or salt thereof is one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride
- a headwear structure, configured to be worn on a surgeon's head during surgery, supporting the headlamp, the headwear structure including an exterior surface;
- the antimicrobial coating additionally applied to the exterior surface of the headwear structure;
- a video camera configured to record a surgery, the video camera including an exterior surface, and the antimicrobial coating applied to the exterior surface of the video camera;
- a cable attached to the headlamp and configured to attach to a power source to power the headlamp, the cable including an exterior surface, and the antimicrobial coating applied to the exterior surface of the cable;
- a color temperature filter attached to the headlamp, the color temperature filter having an exterior surface, and the antimicrobial coating applied to the exterior surface of the color temperature filter; and
- binocular loupes including an exterior surface, and an antimicrobial coating applied to the exterior surface of the binocular loupes.

According to a second aspect of the present disclosure, a method of imparting antimicrobial properties onto an exterior surface of a surgical headlight system comprising: presenting a surgical headlight system including a headlamp including an exterior surface; and applying, to the exterior surface of the headlamp, a solution including a silane quaternary ammonium ion or salt thereof.

Embodiments of the second aspect of the invention can include any one or a combination of the following features:
- the silane quaternary ammonium ion or salt thereof is one or more of: 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride;
- the solution further includes isopropyl alcohol;
- the silane quaternary ammonium ion or salt thereof is between 0.1 percent and 10 percent by weight of the solution;
- the isopropyl alcohol is between 30 percent to 90 percent by weight of the solution;
- the surgical headlight system further including a headwear structure, configured to be worn on a surgeon's head during surgery, supporting the headlamp, the headwear structure including an exterior surface, applying the solution to the exterior surface of the headwear structure;
- the surgical headlight system further including a video camera configured to record a surgery, the video camera including an exterior surface, and applying the solution to the exterior surface of the video camera; and
- the surgical headlight system further including a cable attached to the headlamp and configured to attach to a power source to power the headlamp, the cable including an exterior surface, and applying the solution to the exterior surface of the cable.

These and other features, advantages, and objects of the present invention will be further understood and appreciated by those skilled in the art by reference to the following specification, claims, and appended drawings.

DETAILED DESCRIPTION

For purposes of description herein, it is to be understood that the specific devices and processes illustrated in the attached drawings, and described in the following specification are simply exemplary embodiments of the inventive concepts defined in the appended claims. Hence, physical characteristics relating to the embodiments disclosed herein are not to be considered as limiting, unless the claims expressly state otherwise.

Figure 1:
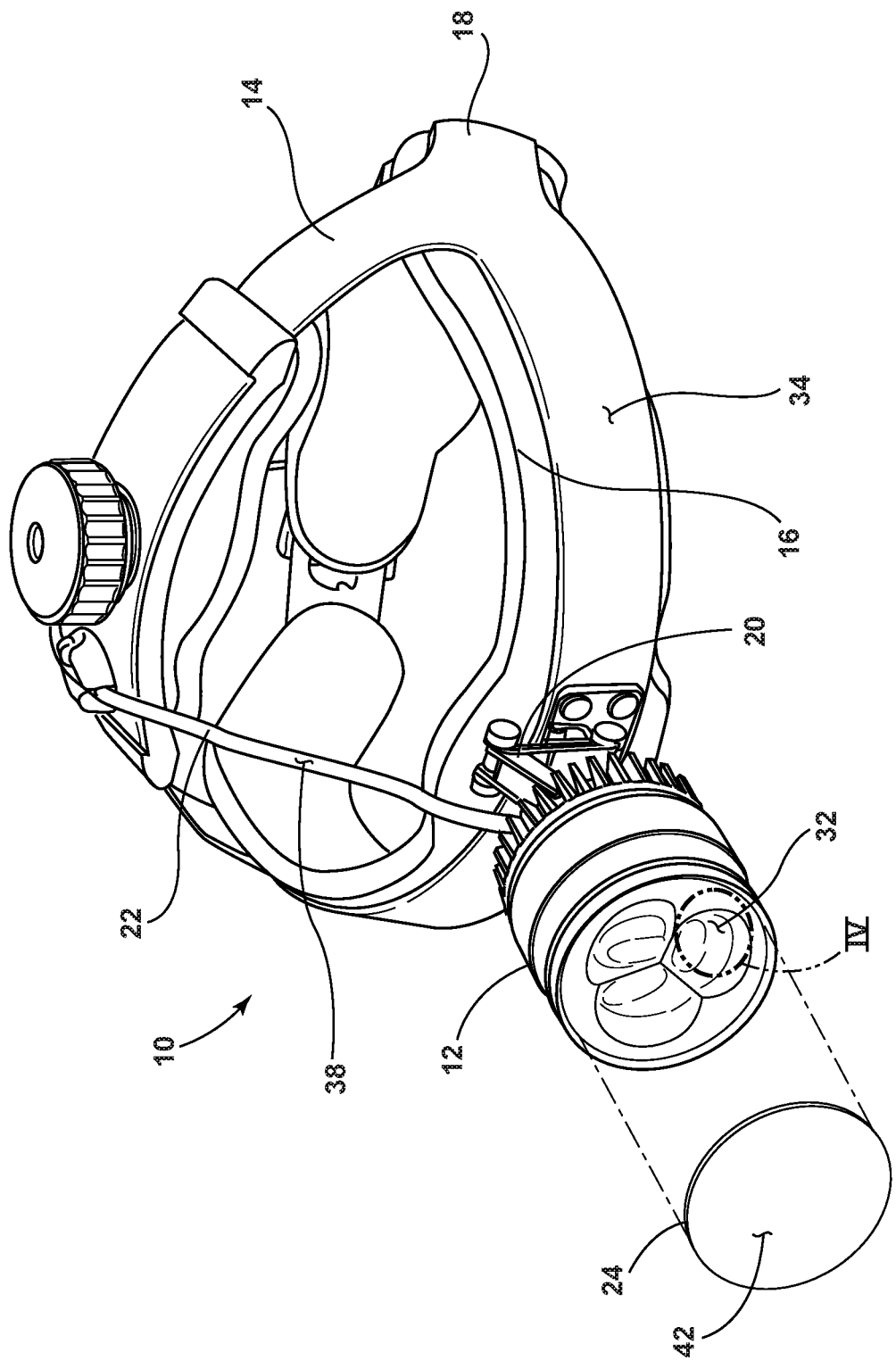
FIG. 1 is a perspective view of a first embodiment of a surgical headlight system, illustrating a headlamp with an exterior surface included thereon.

Referring to FIG. 1, a surgical headlight system 10 includes a headlamp 12. In general terms, the headlamp 12 emits light to illuminate a surgical area on a patient to assist a surgeon in performing a surgical procedure on the patient. The surgical headlight system 10 further includes a headwear structure 14. The headwear structure 14 is configured to be worn on the surgeon's head during surgery. The headwear structure 14 can include padding 16, which adds comfort to the surgeon wearing the surgical headlight system 10, and a more rigid band 18 to extend around the surgeon's head supporting the padding 16 and the headlamp 12. The headwear structure 14 can support the headlamp 12 via an adjustable arm 20 attaching the headlamp 12 to the headwear structure 14. The surgical headlight system 10 can further include a cable 22. The cable 22 is attached to the headlamp 12 and to a power source (not illustrated, such as a battery) and allows the power source to power the headlamp 12 and thus emit light. The cable 22 can be used for any purpose, however. The surgical headlight system 10 can further include a color temperature filter 24 removably attached to the headlamp 12. The color temperature filter 24 can alter the light emitted by the headlamp 12 so that the light illuminating the surgical area is more beneficial to the surgeon.

Figure 2:
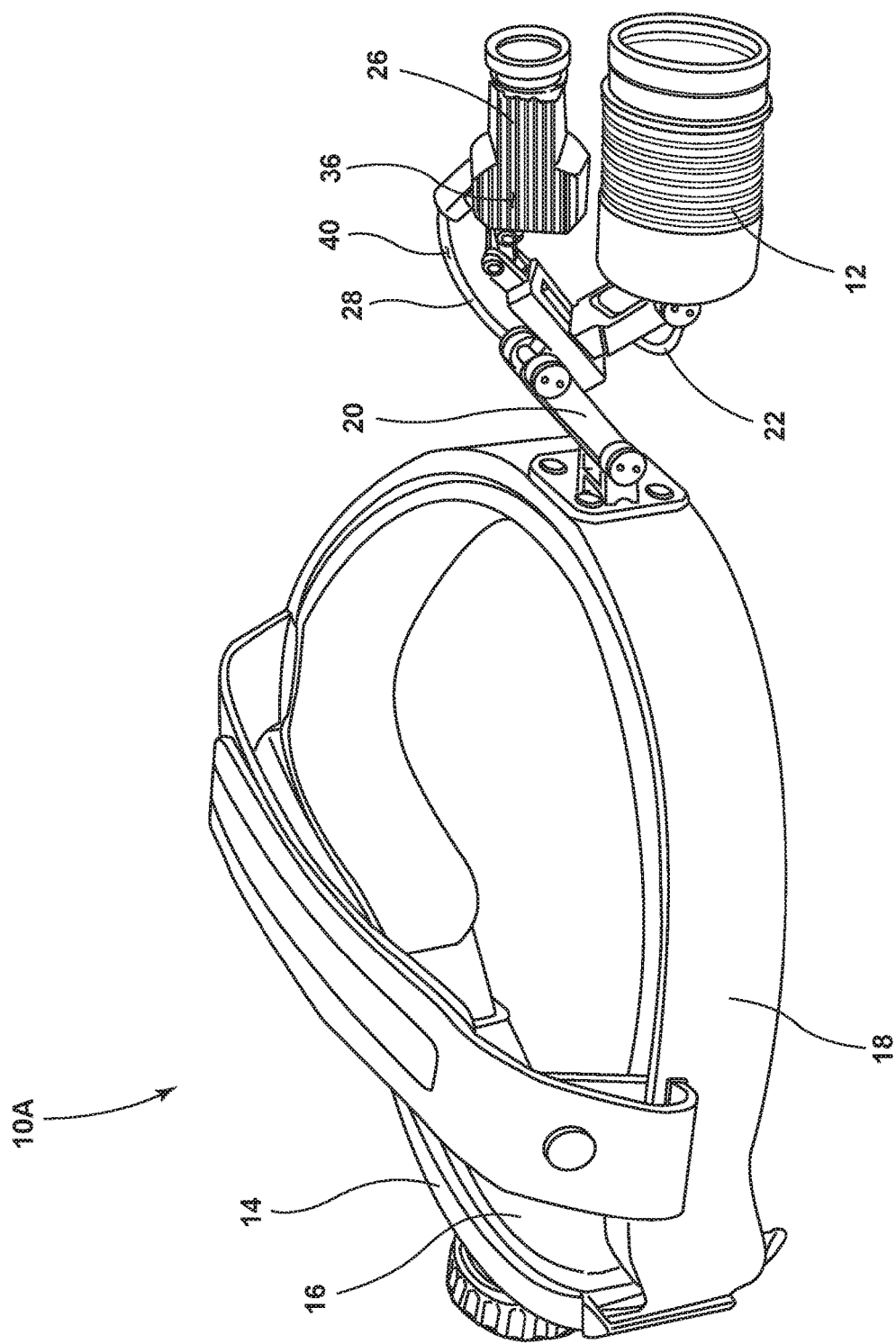
FIG. 2 is a perspective view of a second embodiment of a surgical headlight system, illustrating a video camera with an exterior surface included thereon.

Referring now to FIG. 2, another surgical headlight system 10A is illustrated. This surgical headlight system 10A, like surgical headlight system 10, includes a headwear structure 14 (including padding 16 and a more rigid band 18) supporting a headlamp 12 via an adjustable arm 20. As before, a cable 22 connects the headlamp 12 to a power source (again not illustrated). The surgical headlight system 10A further includes a video camera 26. The video camera 26 is configured to record a surgery and may include a cable 28 for connection to a power source and to transmit data, such as audio and/or video data to an external source.

Figure 3:
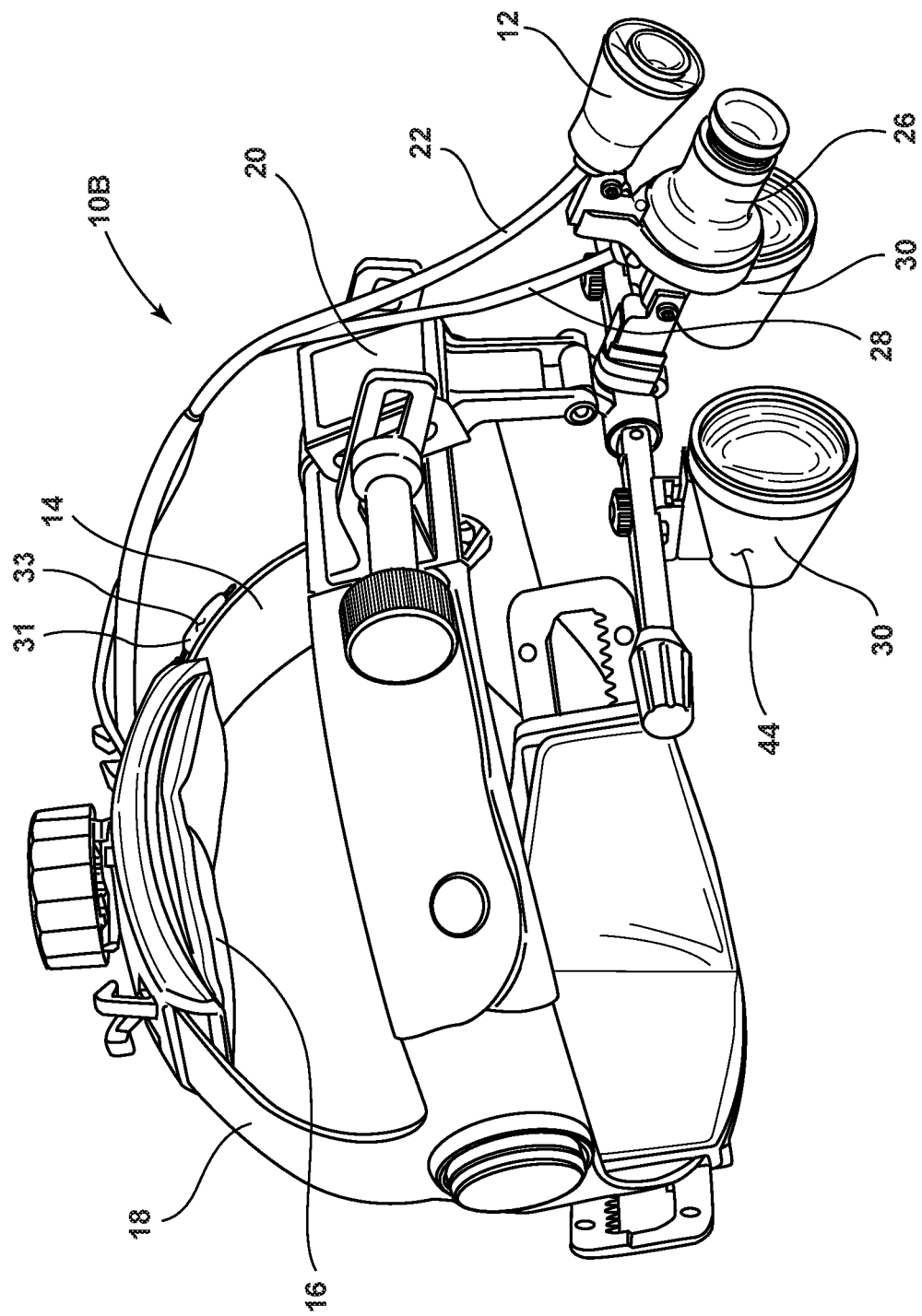
FIG. 3 is a perspective view of a third embodiment of a surgical headlight system, illustrating binocular loupes with an exterior surface included thereon.

Referring now to FIG. 3, another surgical headlight system 10B is illustrated. This surgical headlight system 10B, like surgical headlight systems 10 and 10A, includes a headwear structure 14 (including padding 16 and a more rigid band 18) supporting a headlamp 12 and video camera 26 via an adjustable arm 20. As before, a cable 22 connects the headlamp 12 to a power source (again not illustrated) and a cable 28 connects the video camera 26 to a power source (not illustrated) and can transmit data, such as audio and/or video data to an external source. The surgical headlight system 10B further includes a pair of binocular loupes 30, which magnify the surgical area when the surgeon views through the pair of binocular loupes 30. The adjustable arm 20 additionally connects the binocular loupes 30 to the headwear structure 14. The surgical headlight system 10B further includes a transmitter 31, which can be in communication with the video camera 26 via cable 28 or otherwise and transmit data (such as audio and/or video data) to an external receiver.

The surgical headlight systems 10, 10A, and 10B described above all include a variety of exterior surfaces that may harbor harmful microbes, viruses, bacteria, and the like. For example, headlamp 12 includes an exterior surface 32 (see FIG. 1). Likewise, the headwear structure 14 includes an exterior surface 34, the video camera 26 includes an exterior surface 36 (see FIG. 2), and the cables 22 and 28 each include an exterior surface 38 (see FIG. 1) and 40 (see FIG. 2), respectively. Similarly, the color temperature filter 24 has an exterior surface 42 (see FIG. 1) and the pair of binocular loupes 30 include an exterior surface 44 (see FIG. 3). The transmitter 31 includes an exterior surface 33.

Figure 4:
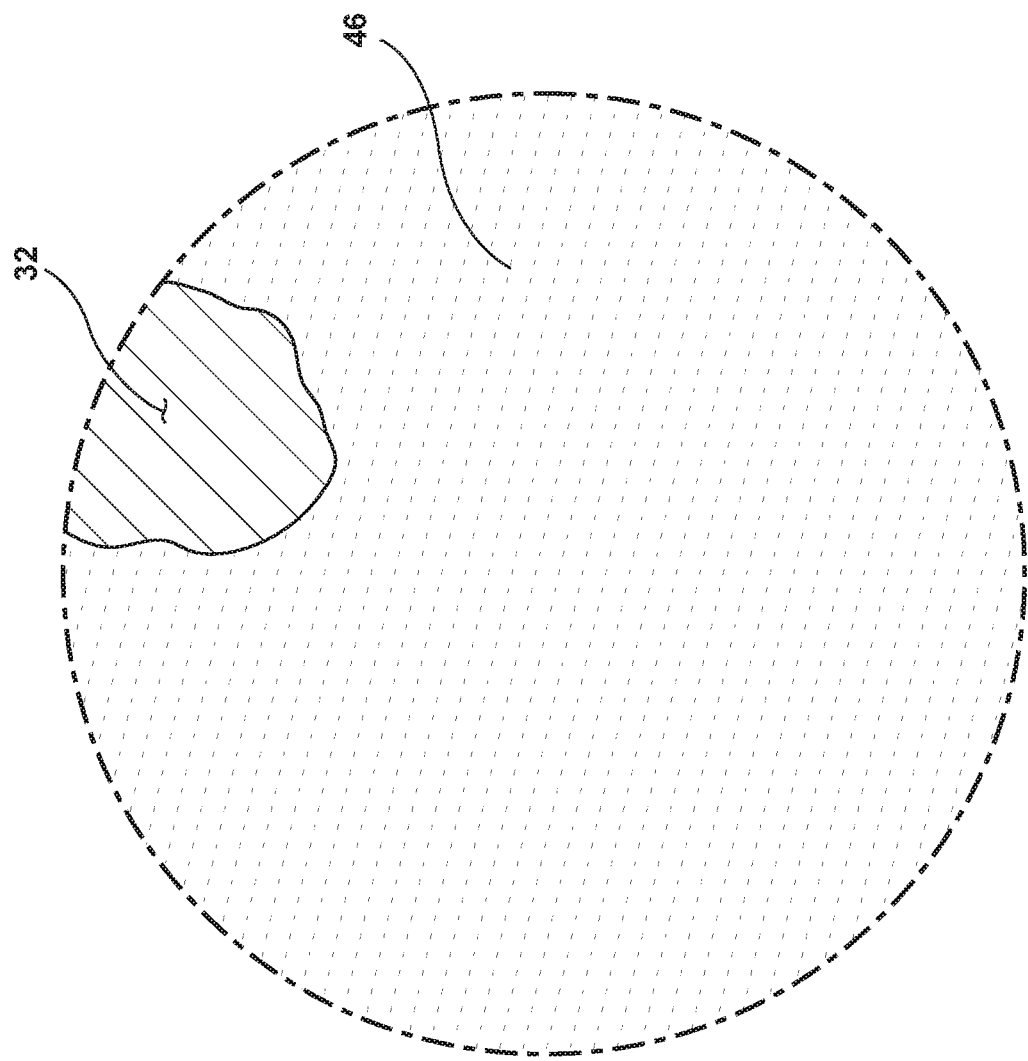
FIG. 4 is a schematic magnified view of area IV from FIG. 1, illustrating an antimicrobial coating applied over the exterior surface of the headlamp of FIG. 1.

Referring now to FIG. 4, the surgical headlight systems 10, 10A, and 10B further include an antimicrobial coating 46 applied to, and at least partially, covering the exterior surface 32 of the headlamp 12. The antimicrobial coating 46 can additionally (or separately) be applied to anything attached to or part of the surgical headlight systems 10, 10A, and 10B. In other words, the antimicrobial coating 46 can be applied to, and at least partially cover, the exterior surface 34 of the headwear structure 14, the exterior surface 36 of the video camera 26, the exterior surface 38 of the cable 22, the exterior surface 40 of the cable 28, the exterior surface 42 of the color temperature filter 24, the exterior surface 44 of the pair of binocular loupes 30, and the exterior surface 33 of the transmitter 31.

The antimicrobial coating 46 includes a silane quaternary ammonium ion or salt thereof. Preferred silane quaternary ammonium ions or salts thereof include 3-(trimethoxysilyl)propyldimethyloctadecyl ammonium ion, 3-(trimethoxysilyl)propyldimethyloctadecyl ammonium chloride, 3-(trihydroxysilyl)propyldimethyloctadecyl ammonium ion, or 3-(trihydroxysilyl)propyldimethyloctadecyl ammonium chloride. Applying the antimicrobial coating 46 to the various exterior surfaces 32, 34, 36, 38, 40, 42, and 44 of the surgical headlight systems 10, 10A, and 10B imparts antimicrobial properties on the various exterior surfaces 32, 34, 36, 38, 40, 42, and 44, which prevents or lessens the ability of said exterior surfaces 32, 34, 36, 38, 40, 42, and 44 to harbor harmful microbes, viruses, bacteria, and the like. Applying the antimicrobial coating 46 to the various exterior surfaces 32, 34, 36, 38, 40, 42, and 44 serves to lessen the ability of the surgical headlight systems 10, 10A, and 10B to act as a vehicle that transmits the harmful microbes, viruses, bacteria, and the like to the patient.

Further described herein is a novel method of imparting antimicrobial properties onto any of the exterior surfaces 32, 34, 36, 38, 40, 42, and 44 of any of the surgical headlight systems 10, 10A, and 10B described above. The method comprises presenting a surgical headlight system 10, 10A, or 10B including the headlamp 12 with the exterior surface 32. The method further comprises applying, to the exterior surface 32 of the headlamp 12, a solution including the silane quaternary ammonium ion or salt thereof, as described above. In addition to the silane quaternary ammonium ion or salt thereof, the solution can further include a solvent. A preferred solvent is isopropyl alcohol.

The silane quaternary ammonium ion or salt thereof can comprise between 0.1 percent and 10 percent by weight of the solution. More preferably, the silane quaternary ammonium ion or salt thereof can comprise between 0.75 percent and 5 percent by weight of the solution. Even more preferably, the silane quaternary ammonium ion or salt thereof can comprise between 1.9 percent and 2.1 percent by weight of the solution.

As for the isopropyl alcohol, the isopropyl alcohol can comprise between 30 percent to 90 percent by weight of the solution. More preferably, the isopropyl alcohol can comprise between 55 percent and 65 percent by weight of the solution. An example preferable solution comprises (by weight) 60.0 percent isopropyl alcohol, 2.02 percent 3-(trimethoxysilyl)propyldimethyloctadecyl ammonium chloride, and 34.19 percent deionized water.

Again, the solution can be applied to any exterior surface of the surgical headlight systems 10, 10A, and 10B described above, including the exterior surface 34 of the headwear structure 14, the exterior surface 36 of the video camera 26, the exterior surface 38 of the cable 22, and so on.

It is to be understood that variations and modifications can be made on the aforementioned structure without departing from the concepts of the present invention, and further it is to be understood that such concepts are intended to be covered by the following claims unless these claims by their language expressly state otherwise.

The invention claimed is:

1. A surgical headlight system comprising:
a headlamp including an exterior surface; and
an antimicrobial coating applied to the exterior surface of the headlamp;
wherein, the antimicrobial coating includes isopropyl alcohol and one or more of: 3-(trihydroxysilyl)propyldimethyloctadecyl ammonium ion, or 3-(trihydroxysilyl)propyldimethyloctadecyl ammonium chloride.

2. The surgical headlight system of claim 1,
wherein, the antimicrobial coating further includes one or more of: 3-(trimethoxysilyl)propyldimethyloctadecyl ammonium ion, or 3-(trimethoxysilyl)propyldimethyloctadecyl ammonium chloride.

3. The surgical headlight system of claim 1 further comprising:
a headwear structure, configured to be worn on a surgeon's head during surgery, supporting the headlamp, the headwear structure including an exterior surface; and
wherein, the antimicrobial coating is additionally applied to the exterior surface of the headwear structure.

4. The surgical headlight system of claim 1 further comprising:
a video camera configured to record a surgery, the video camera including an exterior surface;
wherein, the antimicrobial coating is additionally applied to the exterior surface of the video camera.

5. The surgical headlight system of claim 1 further comprising:
a cable attached to the headlamp, the cable including an exterior surface;
wherein, the antimicrobial coating is additionally applied to the exterior surface of the cable.

6. The surgical headlight system of claim 1 further comprising:
a color temperature filter attached to the headlamp, the color temperature filter having an exterior surface;
wherein, the antimicrobial coating is additionally applied to the exterior surface of the color temperature filter.

7. The surgical headlight system of claim 1 further comprising:
binocular loupes including an exterior surface;
wherein, the antimicrobial coating is additionally applied to the exterior surface of the binocular loupes.

8. The surgical headlight system of claim 1 further comprising:
a transmitter including an exterior surface;
wherein, the antimicrobial coating is additionally applied to the exterior surface of the transmitter.

9. A method of imparting antimicrobial properties onto an exterior surface of a surgical headlight system comprising:
presenting a surgical headlight system including a headlamp including an exterior surface; and
applying, to the exterior surface of the headlamp, a solution including isopropyl alcohol and one or more of: 3-(trihydroxysilyl)propyldimethyloctadecyl ammonium ion, or 3-(trihydroxysilyl)propyldimethyloctadecyl ammonium chloride.

10. The method of claim 9,
wherein, the one or more of: 3-(trihydroxysilyl)propyldimethyloctadecyl ammonium ion, or 3-(trihydroxysilyl)propyldimethyloctadecyl ammonium chloride is between 0.1 percent and 10 percent by weight of the solution.

11. The method of claim 10,
wherein, the isopropyl alcohol is between 30 percent to 90 percent by weight of the solution.

12. The method of claim 11,
the surgical headlight system further including a headwear structure, configured to be worn on a surgeon's head during surgery, supporting the headlamp, the headwear structure including an exterior surface; and
the method further comprising applying the solution to the exterior surface of the headwear structure.

13. The method of claim 11,
the surgical headlight system further including a video camera configured to record a surgery, the video camera including an exterior surface; and
the method further comprising applying the solution to the exterior surface of the video camera.

14. The method of claim 11,
the surgical headlight system further including a cable attached to the headlamp, the cable including an exterior surface; and
the method further comprising applying the solution to the exterior surface of the cable.

15. A surgical headlight system comprising:
a headwear structure;
an adjustable arm attached to the headwear structure;
a headlamp connected to the adjustable arm; and
binocular loupes connected to the adjustable arm;
wherein, each of the headwear structure, the headlamp, and the binocular loupes include an exterior surface and an antimicrobial coating applied to the exterior surface; and
wherein, the antimicrobial coating comprises one or more of:
3-(trimethoxysilyl)propyldimethyloctadecyl ammonium ion,
3-(trimethoxysilyl)propyldimethyloctadecyl ammonium chloride,
3-(trihydroxysilyl)propyldimethyloctadecyl ammonium ion, or
3-(trihydroxysilyl)propyldimethyloctadecyl ammonium chloride.

* * * * *